United States Patent [19]

Connor et al.

[11] Patent Number: 4,775,677

[45] Date of Patent: Oct. 4, 1988

[54] [3-SUBSTITUTED-2-(SUBSTITUTED IMINO)-4-OXO-5-THIAZOLIDINYLIDENE]ACETIC ACIDS HAVING ACTIVITY AS LEUKOTRIENE ANTAGONISTS

[75] Inventors: David T. Connor; Roderick J. Sorenson, both of Ann Arbor, Mich.

[73] Assignee: Warner-Lambert Company, Morris Plains, N.J.

[21] Appl. No.: 946,689

[22] Filed: Jan. 6, 1987

Related U.S. Application Data

[63] Continuation of Ser. No. 733,174, May 13, 1985, abandoned.

[51] Int. Cl.[4] .................. C07D 277/54; A61K 31/425
[52] U.S. Cl. ...................................... 514/369; 548/184
[58] Field of Search ........................ 548/184; 514/369

[56] References Cited

U.S. PATENT DOCUMENTS 3,873,524  3/1925  Sellstedt .............................. 548/184

OTHER PUBLICATIONS

Chem. Abstr., Mushralo et al., 48, 13692g.
Merck Index, 9th Edition, 1976 pp. 857, 859 and 860.
Melika et al., *Uhr. Khin. Zh.*, vol. 32 (9), pp. 1006–1008, (1966).
Nagorajan et al., *Proc. Ind. Acad. Sci.*, vol. 92 (1), pp. 99–106 (1983).
Nagase, H., *Chem. Pharm. Bull.*, vol. 21 (2), pp. 270–278, (1973).
Nagase, H., *Chem. Pharm. Bull.*, vol. 21 (5), pp. 1132–1135, (1973).
Vogeli et al., *Helvetica Chimica. Acta.*, vol. 61, Fasc. 2, No. 49, pp. 607–617, (1978).
Acheson et al., *J. C. S.*, Perkin I, pp. 415–422, (1981).

*Primary Examiner*—Robert Gerstl
*Attorney, Agent, or Firm*—Joan Thierstein

[57] ABSTRACT

The present invention provides novel [3-substituted-2-(substituted imino)-4-oxo-5-thiazolidinylidene]acetic acids, and novel pharmaceutical compositions and methods of use thereof. The novel acids of the invention are leukotriene antagonists having activity useful for treating asthma, allergies, cardiovascular diseases, migraines, and inflammation.

32 Claims, No Drawings

4,775,677

[3-SUBSTITUTED-2-(SUBSTITUTED IMINO)-4-OXO-5-THIAZOLIDINYLIDENE]ACETIC ACIDS HAVING ACTIVITY AS LEUKOTRIENE ANTAGONISTS

The present application is a continuation of U.S. Ser. No. 06/733,174 filed May 13, 1985, now abandoned.

BACKGROUND OF THE INVENTION

The present invention provides novel [3-substituted-2-(substituted imino)-4-oxo-5-thiazolidinylidene]acetic acids, and novel pharmacological compositions and methods of use thereof. The novel acids of the present invention are leukotriene antagonists having activity useful for treating asthma, allergies, cardiovascular diseases, migraines, and inflammation.

U.S. Pat. No. 3,873,524 discloses compounds of formula XL wherein $R^{20}$ and $R^{21}$ are lower alkyl of from one to six carbons. The compounds XL are disclosed as intermediates for the preparation of compounds useful in pharmacology but do not teach either pharmacological or biological activity for the intermediates themselves. Additionally the only species disclosed are compounds of Formula XL wherein $R^{20}$ and $R^{21}$ are methyl. On the other hand the compounds of the present invention are compounds having Formula I wherein $R_1$ and $R_2$ are alkyl of from five carbons to at least seven carbons or more and moreover the compounds wherein $R_1$ and $R_2$ are alkyl of five, six, seven, and eight carbons which are closest to the disclosure of U.S. Pat. No. 3,873,524 are now found to have pharmacological activity which is unexpected and surprising.

R. M. Acheson and J. D. Wallis disclose compounds of Formula XLI wherein $R^{22}$ and $R^{23}$ are the same and are methyl or phenyl in "Addition Reactions of Heterocyclic Compounds. Part 74. Products from Dimethyl Acetylenedicarboxylate with Thiourea, Thioamide, and Guanidine," *J. C. S. Perkin I* pp. 415-422 (1981). No utility is disclosed for the esters of Formula XLI by Acheson et al and present compounds of Formula I having pharmacological activity are not within the teachings to these esters.

Similarly, U. Vogeli and W. von Phillipson teach esters of the Formula XLII wherein p-Brph is p-bromophenyl, Bzl is benzyl, Ph is phenyl and Me is methyl in "49. Structures of Addition Products of Acetylenedicarboxylic Acid Esters with Various Dinucleophiles. An Application of C,H-Spin-Coupling Constants," *Helvetica Chimica Acta*, Vol. 61, Fasc 2 (1978)-Nr 49. Again the present compounds having utility in pharmacology are not taught by Vogeli et al as there is neither a teaching to dihalo or trihalo phenyl in the $R_1$ or $R_2$ position of the Formula I nor a teaching to a utility.

H. Nagase, "Studies on Fungicides. XXI. Reaction of Dimethyl Acetylenedicarboxylate with Thioureas," *Chem. Pharm. Bull.* 21(2), 270–278 and 1132–1135 (1973) discloses a compound within the Formula XLII noted above but limited to benzyl substituents on the nitrogens. Again the compounds of the present invention having utility in pharmacology are not taught. Melika, et al, "Derivatives of 4-Thiazolinone and 4-Thiazolidinone based on some Acetylenecarboxylic acids," *Uhr. Khim. Zh.* 32(9), 1006-1008 (1966) of C.A. 66: 28704u (1967) also disclose an ester similar to the Formula XLII and further limited to a phenyl group on the imino nitrogen and an α-naphthyl on the remaining nitrogen.

Nagarajan et al "Addition Products of Dimethyl Acetylenedicarboxylate to Thiourea Studies on 2-(p-bromophenyl)imino-3-methyl-5-carbomethoxymethylenethiazolidin-4-one" of *C.A* 100: 209430z (1964) discloses a compound of Formula XLIII not included in the present invention and not teaching the compound of Formula I now having been found to be useful pharmacological agents.

SUMMARY OF THE INVENTION

The present invention is a compound of Formula 1 wherein $R_1$ and $R_2$ are the same or different and are
  (a) alkyl of from five to 12 carbons, inclusive;
  (b) aryl having the structure X wherein n is a number from zero to three, inclusive; such that (i) where n is one then Q is alkyl of from one to four carbons, inclusive; or alkoxy of from one to four carbons, inclusive; (ii) where n is two or three then Q is the same or different and is alkyl of from one to four carbons, inclusive; alkoxy of from one to four carbons; or halogen; and (iii) where n is one, two, or three then Q is also nitro or amino, optionally substituted by lower alkyl of from one to four carbons, inclusive;
  (c) aralkyl wherein ar is aryl having the structure X wherein n is a number of from zero to three and Q is defined above, and alkyl is of from one to four carbons, inclusive; or
  (d) cycloalkyl of from three to seven carbons, inclusive;
  (e) adamantyl, or
  (f) naphthyl and pharmaceutically acceptable salts thereof, with the proviso that if $R_1$ and $R_2$ are the same then n cannot be zero and also with the proviso that when $R_1$ and $R_2$ are different then $R_2$ cannot be alkyl or aralkyl.

The preferred compounds of the present invention are:
[3-octyl-2-(octylimino)-4-oxo-5-thiazolidinylidene]acetic acid;
[3-pentyl-2-(penytlimino)-4-oxo-5-thiazolidinylidene]acetic acid;
[3-hexyl-2-(hexylimino)-4-oxo-5-thiazolidinylidene]acetic acid;
[2-[(3,4-dichlorophenyl)imino]-3-hexyl-4-oxo-5-thiazolidinylidene]acetic acid;
[3-hexyl-2-[(1-naphthalenyl)imino]-4-oxo-5-thiazolidinylidene]acetic acid;
[3-heptyl-2-(heptylimino)-4-oxo-5-thiazolidinylidene]acetic acid;
[4-oxo-3-(3,4-dichlorophenyl)-2-[(3,4-dichlorophenyl)imino]-5-thiazolidinylidene]acetic acid;
4-oxo-3-(3,4-dibromophenyl)-2-[(3,4,-dibromophenyl)imino]-5-thiazolidinylidene]acetic acid;
4-oxo-3-(3,4,5-trichlorophenyl)-2-[3,4,5-trichlorophenyl)imino]-5-thiazolidinylidene]acetic acid.

The present invention also includes a pharmaceutical composition comprising an amount effective for treating asthma, allergies, cardiovascular disorders, migraine, or inflammation, of a compound of Formula I wherein $R_1$ and $R_2$ are as defined above, or pharmaceutically acceptable salt thereof in admixture with a pharmaceutically acceptable carrier.

Further, the invention is a method of treating asthma, allergies, cardiovascular disorders, migraine, or inflammation by administering to a mammal, including a human, suffering therefrom an effective amount of a compound of Formula I wherein $R_1$ and $R_2$ are as defined above, or a pharmaceutically acceptable salt thereof.

DETAILED DESCRIPTION OF THE INVENTION

The term "alkyl of from five to twelve carbons, inclusive," as used herein includes pentyl, hexyl, heptyl, octyl, nonyl, decyl, undecyl, dodecyl, and the isomers thereof. Of these the more preferred are alkyl of from five to eight, inclusive.

The term "alkyl of from one to four carbons, inclusive," as used herein includes methyl, ethyl, propyl, butyl, and isomers thereof.

The term "alkoxy of from one to four carbons, inclusive," as used herein includes methoxy, ethoxy, propoxy, butyloxy, and isomers thereof.

The term "halogen" as used herein is bromo, iodo, chloro, fluoro, or trifluoromethyl.

The term "monosubstituted phenyl" includes, for example, 2-propoxyphenyl, 3-methylphenyl, 4-methoxyphenyl, 2-pentylphenyl, and the like.

The term "disubstituted phenyl" includes, for example, 3,4-dichlorophenyl; 2,4-dimethoxyphenyl; 2,5-ditertiarybutylphenyl; 3-chloro-4-pentylphenyl and the like.

The term "trisubstituted phenyl" includes, for example, 2,3,4-tripropylphenyl; 2-fluoro-3,4-diethoxyphenyl and the like.

The term "naphthalenyl" includes 1-naphthyl, 2-naphthyl, 3-naphthyl and the like.

The pharmacologically acceptable salt of the present invention may be those readily prepared with inorganic and organic bases, such as NaOH, KOH, Mg(OH)$_2$, Ca(OH)$_2$, NH$_4$OH, substituted ammonium salts, L-arginine, choline, N-methylglucamine and the like.

The usefulness of the compounds of Formula I is particularly directed to the treatment of humans. By virtue of the activity of the compounds having the Formula I of the present invention as antagonists of Slow Reacting Substance of Anaphylaxis (leukotrienes C, D, and E) are useful in the treatment of allergic rhinitis, asthma, bronchitis, and urticaria. They are also particularly useful for the treatment of cardiovascular diseases mediated by leukotrienes, C, D, and E. See B. Samuelsson, "Leukotrienes: Mediators of Immediate Hypersensitivity Reactions and Inflammation,"*Science*, Vol. 220, p. 568 (1983); P. J. Piper, "Leukotrienes," *Trends in Pharmaceutic Sciences*, pp. 75–77 (1983; and J. L. Romson, et al, "Reduction of the Extent of Ischemic Myocardial Injury by Neutrophil Depletion in the Dog," *Circulation*, Vol. 67, p. 1016 (1983). The activity of the compounds I of the present invention is determined in a leukotriene receptor binding assay (RBL-1) described by R. F. Bruns, W. J. Thomsen, and T. A. Pugsley in *Life Sciences*, 33, p. 645 (1983).

The antiasthma and antiallergic activity provides methods of treatment for hypersensitivity reactions having broad symptoms. For example, the symptoms may include dermatitis, lacrimation, nasal discharge, coughing, sneezing, nausea, vomiting, diarrhea, difficulty in breathing, pain, inflammation, and in severe cases, anaphylactic shock and circulatory collapse. The symptoms may be found in man as well as other animals suffering from bronchial asthma, seasonal pollinosis (e.g., hayfever), allergic rhinitis, urticaria, allergic conjunctivitis, food allergies, and anaphylactoid reactions.

Likewise, the activity of the compounds of Formula I provides a method of treatment for cardiovascular disorders. The symptoms of a subject having a cardiovascular disorder may be determined by special diagnostic procedures directed to subjects having a history, general physical appearance and then detailed deviations from normal appearances suggesting a cardiovascular disorder. Such disorders are particularly found in man as well as other mammals. Symptoms of the disorders are described extensively in *The Merck Manual* 14th ed, (1982).

Further, methods of treatment are provided by the compounds of Formula I herein for migrane and inflammation. The symptoms requiring treatment for these purposes are readily recognized particularly for migraine in man and/or inflammation in man.

Pharmaceutical compositions which are also the present invention are prepared from the compound of Formula I and salts thereof described as the present invention having inert pharmaceutical carriers. The compositions may be either solid or liquid.

A physician or veterinarian of ordinary skill readily determines a subject who is exhibiting symptoms described herein. Regardless of the route of administration selected, the compounds of the present invention are formulated into pharmaceutically acceptable dosage forms by conventional methods known to the pharmaceutical art.

The compounds can be administered in such oral unit dosage forms such as tablets, capsules, pills, powders, or granules. They also may be administered rectally or vaginally in such forms as suppositories or bougies; they may also be introduced parenterally (e.g., subcutaneously, intravenously, or intramuscularly), using forms known to the pharmaceutical art. They are also introduced directly to an affected area, (e.g., in the form of a topical, of eye drops or for inhalation). For the treatment of asthma or allergies such as erythema, the compounds of the present invention may preferably be administered topically in the form of ointments, creams, gels, or the like. However, in general, the preferred route of administration is orally.

An effective but nontoxic quantity of the compound is employed in treatment. The ordinarily skilled physician or veterinarian will readily determine and prescribe the effective amount of the compound to prevent or arrest the progress of the condition for which treatment is administered. In so proceeding, the physician or veterinarian could employ relatively low dosages at first, subsequently increasing the dose until a maximum response is obtained.

Initial dosages of the compounds of the invention having Formula I are ordinarily in the area of 5 mg up to 1 g per day orally, preferable 50 mg to 300 mg per dose orally, given from one to four times daily or as needed. When other forms of administration are employed equivalent doses are administered.

Generally, the compounds having the Formula I wherein $R_1$ and $R_2$ are as defined above are prepared by stirring a mixture of acetylenedicarboxylic acid and a compound of Formula II wherein $R_1$ and $R_2$ are as defined above at room temperature in an organic solvent such as methanol, tetrahydrofuran, acetonitrile, and the like for from two to 16 hours (see Scheme I). Also, a similar general synthesis using the above conditions or conditions varying only within the skill of an artisan from those described above may be accomplished using the lower alkyl esters (of from one to four carbons) of acetylenedicarboxylic acid to produce penultimate intermediate of Formula V wherein $R_1$ and $R_2$ are as defined above and $R_3$ is lower alkyl of from one to four carbons (see Scheme II). The penultimate intermediate V is then treated with lithium halide, preferably iodide, in an organic solvent such as dimethylformamide, dimethylacetamide, dimethylsulfoxide, and the like to cleave the ester group $R_3$ and produce the desired compound of Formula I of the present invention. The method of Scheme II is preferable for compounds of Formula I where $R_1$ and $R_2$ are selected from the phenyl; mono-, di-, or trisubstituted phenyl; and naphthyl groups.

The compounds of Formula II in Scheme I and II may, generally, be prepared by heating a mixture of one equivalent of an amine substituted appropriately and an equivalent corresponding isothiocyanate in a solvent toluene, xylene, benzene, and the like from 50° to 140° C. preferrable about 100° C. for from six to 24 hours. See Schemes III and IV.

The products of the reactions described herein are isolated by conventional means such as extraction, distillation, chromatography, and the like.

DESCRIPTION OF THE PREFERRED EMBODIMENTS

The process of this invention is further elaborated by the representative examples as follows.

EXAMPLE 1

[3-Octyl-2-(octylimino)-4-oxo-5-thiazolidinylidene]acetic acid

A mixture of acetylenedicarboxylic acid (7.2 g, 60 mmoles) and N,N'-dioctylthiourea (18 g, 60 mmoles) in methanol (300 mls) is stirred at room temperature for 16 hours. The solvent is removed under reduced pressure to leave a syrupy residue which eventually crystallizes. Recrystallization from acetonitrile gave the product (18 g), mp 57°–61° C.

EXAMPLE 2

[3-Ethyl-2-(ethylimino)-4-oxo-5-thiazolidinylidene]acetic acid

Prepared by the method described in Example 1 from N,N'-diethylthiourea (1.0 g, 8 mmoles) and acetylenedicarboxylic acid (1 g, 9 mmoles). Crystallization from hexane gave the product (1.5 g), mp 148°–152° C.

EXAMPLE 3

[3-Pentyl-2-(pentylimino)-4-oxo-5-thiazolidinylidene]acetic acid

Prepared by the method described in Example 1 from N,N'-dipentylthiourea (31.4 g, 150 mmoles) and acetylenedicarboxylic acid (17.1 g, 150 mmoles). Recrystallization from acetonitrile gave the product (20.6 g), mp 85°–88° C.

EXAMPLE 4

[3-Hexyl-2-(hexylimino)-4-oxo-5-thiazolidinylidene]acetic acid

Prepared by the method described in Example 1 from N,N'-dihexylthiourea (114.2 g, 468 mmoles) and acetylenedicarboxylic acid (53.4 g, 468 mmoles). Recrystallization from acetonitrile gave the product (50.4 g) mp 66°–69° C.

EXAMPLE 5

[4-Oxo-3-(3,4-dimethylphenyl)-2-dimethylphenyl)imino]-5-thiazolidinylidene]acetic acid Prepared by the method described in Example 1 from N,N'-diphenylthiourea (25.3 g, 89 mmoles) and acetylenedicarboxylic acid (10.2 g, 89 mmoles). Recrystallization from methanol gave the product (9.8 g), mp 215°–216° C.

EXAMPLE 6

[4-Oxo-3-(3,4,5-trimethoxyphenyl)-2-[(3,4,5-trimethoxyphenyl)imino]-5-thiazolidinylidene]acetic acid Prepared by the method described in Example 1 from N,N'-bis(3,4,5-trimethoxyphenyl)thiourea (26.8 g, 66 mmoles) and acetylenedicarboxylic acid (9.8 g, 86 mmoles). Recrystallization from ethanol gave the product (19 g), mp 250°–252° C.

EXAMPLE 7

[4-Oxo-3-(4-methoxyphenyl)-2-[(4-methoxyphenyl)imino]-5-thiazolidinylidene]acetic acid Prepared by the method described in Example 1 from N,N'-bis(4-methoxyphenyl)thiourea (11.5 g, 40 mmoles) and acetylenedicarboxylic acid (4.6 g, 40 mmoles). Recrystallization from methanol gave the product (10.1 g), mp 184°–187° C.

EXAMPLE 8

[4-Oxo-3-propyl-2-(propylimino)-5-thiazolidinylidene]acetic acid

Prepared by the method described for Example 1 from N,N'-dipropylthiourea (16.0 g, 0.1 m). Recrystallization from isopropyl ether gives white crystals (22.5 g), mp 101°–103° C.

EXAMPLE 9

[3-Butyl-2-(butylimino)-4-oxo-5-thiazolidinylidene]acetic acid

Prepared by the method described for Example 1 from N,N'-dibutylthiourea (7.52 g, 0.04 m). Recrystallization from cyclohexane gives white crystals (9.7 g), mp 99°–101° C.

EXAMPLE 10

[3-(2-Methoxyphenyl)-2-[(2-methoxyphenyl)imino]-4-oxo-5-thiazolidinylidene]acetic acid Prepared by the method described for Example 1 from N,N'-2-methoxyphenylthiourea (14.4 g, 0.05 m). Recrystallization from ethyl acetate gives orange crystals (9.3 g), mp 189°–190° C.

EXAMPLE 11

[2-[(3,4-dichlorophenyl)imino]-3-hexyl-4-oxo-5-thiazolidinylidene]acetic acid

Prepared by the method described in Example 1 from N-hexyl-N'-(3,4-dichlorophenyl)thiourea (5.4 g, 18 mmoles) and acetylenedicarboxylic acid (2.1 g, 17 mmoles). Recrystallization from acetonitrile then methanol gave the product (1 g), mp 156°–157° C.

EXAMPLE 12

[2-[(3,4-dichlorophenyl)imino]-3-methyl-4-oxo-5-thiazolidinylidene]acetic acid

Prepared by the method described in Example 1 from N-methyl-N'-(3,4-dichlorophenyl)thiourea (4.9 g, 21 mmoles) and acetylenedicarboxylic acid (2.6 g, 22 mmoles). Recrystallization from ethyl acetate gave the product (4.5 g), mp 225°–226° C.

EXAMPLE 13

[3-Hexyl-4-oxo-2-(phenylimino)-5-thiazolidinylidene]acetic acid

Prepared by the method described in Example 1 from N-hexyl-N'-phenylthiourea (3.4 g, 14 mmoles) and acetylenedicarboxylic acid (1.7 g, 14 mmoles). Recrystallization from acetonitrile gave the product (3.0 g), mp 145°–146° C.

EXAMPLE 14

[3-(1-Naphthyl)-2-[(1-naphthyl)imino]-4-oxo-5-thiazolidinylidene]acetic acid

Prepared by the method described in Example 1 from N,N'-bis(1-naphthyl)thiourea. Recrystallization from ethyl acetate gave the product mp 250°–253° C.

EXAMPLE 15

[4-Oxo-3-(2-phenylethyl)-2-[(2-phenylethyl)imino]-5-thiazolidinylidene]acetic acid Prepared by the method described in Example 1 from N,N'-bis(2-phenylethyl)thiourea (20.0 g, 0.11 moles) and acetylenedicarboxylic acid (12.7 g, 0.11 moles). Rinsing the crude precipitate with toluene then hexane gave the product (22 g), mp 148°–149° C.

EXAMPLE 16

[3-Undecyl-2-(undecylimino)-4-oxo-5-thiazolidinylidene]acetic acid

Acetylenedicarboxylic acid (4.8 g, 40 mmoles) is added to a warm solution of N,N'-diundecylthiourea (15.0 g, 39 mmoles) in methanol (200 mls) and tetrahydrofuran (100 mls). The mixture is stirred for 16 hours at ambient temperature, then concentrated under reduced pressure and cooled. The precipitate is filtered off, rinsed with cold methanol and dried. Recrystallization from methanol afforded the product (15.3 g), mp 67°–68° C.

EXAMPLE 17

[3-Hexyl-2-[(1-naphthalenyl)imino]-4-oxo-5-thiazolidinylidene]acetic acid

Prepared by the method described in Example 16 from N-hexyl-N'-1-naphthalenylthiourea (8.0 g, 28 mmoles) and acetylenedicarboxylic acid (3.4 g, 28 mmoles). Recrystallization from acetonitrile gave the product (7.1 g), mp 144°–145° C.

EXAMPLE 18

[3-Heptyl-2-(heptylimino)-4-oxo-5-thiazolidinylidene]acetic acid

Prepared by the method described in Example 16 from N,N'-diheptylthiourea (18.0 g, 66 mmoles) and acetylenedicarboxylic acid (8.0 g, 66 mmoles). Recrystallization from acetonitrile gave the product (21.5 g), mp 80°–81° C.

EXAMPLE 19

[3-Decyl-2-(decylimino)-4-oxo-5-thiazolidinylidene]acetic acid

Prepared by the method described in Example 16 from N,N'-didecylthiourea (15.0 g, 42 mmoles) and acetylenedicarboxylic acid (5.0 g, 42 mmoles). Recrystallization from hexane gave the product (17.7 g), mp 68°–69° C.

EXAMPLE 20

[3-Dodecyl-2-(dodecylimino)-4-oxo-5-thiazolidinylidene]acetic acid

Prepared by the method described in Example 16 from N,N'-didodecylthiourea (25.0 g, 61 mmoles) and acetylenedicarboxylic acid (7.3 g, 61 mmoles). Recrystallization from 2-propanol, then ethyl acetate gave the product (24.8 g), mp 71°–72° C.

EXAMPLE 21

[4-oxo-3-(3,4-dichlorophenyl)-2-[(3,4-dichlorophenyl)imino]-5-thiazolidinylidene]acetic acid A mixture of acetylenedicarboxylic acid (6.6 g, 55 mmoles) and N,N'-bis(3,4-dichlorophenyl)thiourea (20.0 g, 55 mmoles) in methanol (400 mls) is stirred at room temperature for 16 hours. The suspended solid is filtered off and rinsed with cold methanol. The solid is then rinsed repeatedly with boiling CH$_2$Cl$_2$ and filtered off. The combined dichloromethane filtrates are concentrated and cooled to afford the crystalline product (7.6 g), mp 221°–222° C.

EXAMPLE 22

[4-Oxo-3-(3,4-dibromophenyl)-2-[(3,4-dibromophenyl)imino]-5-thiazolidinylidene]acetic acid Prepared by the method described in Example 21 from N,N'-bis(3,4-dibromophenyl)thiourea (13.7 g, 25 mmoles) and acetylenedicarboxylic acid (2.7 g, 25 mmoles). Recrystallization from methanol gave the product (2.1 g), mp 235°–237° C.

EXAMPLE 23

[4-Oxo-3-(3,4,5-trichlorophenyl)-2-[3,4,5-trichlorophenyl)imino]-5-thiazolidinylidene]acetic acid Acetylenedicarboxylic acid (5.0 g, 41 mmoles) is added to a warm solution of N,N'-bis(3,4,5-trichlorophenyl)thiourea (20.0 g, 41 mmoles) in methanol (200 mls) and tetrahydrofuran (100 mls). The mixture is stirred at ambient temperature for 16 hours, and the resulting precipitate is filtered off and rinsed with methanol. The filtrate is concentrated and cooled. The precipitate is filtered off, rinsed with methanol and dried. Recrystallization from methanol, then acetonitrile gave the product (2.4 g), mp 255°–257° C.

EXAMPLE 24

[3-(3-Methoxyphenyl)-2-[(3-methoxyphenyl)imino]-4-oxo-5-thiazolidinylidene]acetic acid (I) and sym-di-3-methoxyphenylurea (II)

A mixture of N,N'-3-methoxyphenylthiourea (14.5 g, 0.05 m) and acetylenedicarboxylic acid (22.8 g, 0.2 m) in methanol (500 ml) is stirred at room temperature for five hours. The methanol is removed under reduced pressure to give a yellow residue. Recrystallization from ethyl acetate gives two crops.

1. N,N'-3-methoxyphenylurea II as white crystals (0.71 g, 5%), mp 168°–169° C.
2. I as yellow crystals (2.5 g, 13%), mp 150°–153° C.

EXAMPLE 25

[3-Cyclohexyl-2-(cyclohexylimino)-4-oxo-5-thiazolidinylidene]acetic acid

A mixture of methyl [3-cyclohexyl-2-(cyclohexylimino)-4-oxo-5-thiazolidinylidene]acetate (5.0 g, 14 mmoles) and anhydrous lithium iodide (7.6 g, 57 mmoles) in N,N-dimethylformamide (30 mls) is heated under argon to reflux. After six hours the mixture is cooled, diluted with water, acidified with 4N HCl, and extracted twice with dichloromethane. The combined extracts are washed with brine and dried over MgSO$_4$. The solvent is removed to afford a syrupy residue which evenually crystallizes. Recrystallization from acetonitrile gave the product (3.2 g), mp 189°–190° C.

GENERAL PROCEDURE FOR THE SYNTHESIS OF THIOUREAS (A)

A mixture of amine (1 equivalent) and the corresponding isothiocyanate (1 equivalent) in toluene is heated at 100° for six to 24 hours. The reaction mixture is cooled and the product filtered off. The compounds prepared by this method are listed in Table 2. See Scheme III and IV.

TABLE 1

The following compounds are prepared by the methods described in general procedure A.

$$\text{RNHCNHR} \atop \overset{S}{\|}$$

| Example | R | mp (°C.) |
|---|---|---|
| 26 | CH$_3$(CH$_2$)$_6$ | 56–58 |
| 27 | CH$_3$(CH$_2$)$_9$ | 69–70 |
| 28 | Cyclohexyl | 180–182 |
| 29 | 4-MeO phenyl | 194–196 |
| 30 | 3-MeO phenyl | 125–126 |
| 31 | 2-MeO phenyl | 138–139 |
| 32 | 4-Cl phenyl | 178–179 |
| 33 | 4-Br phenyl | 192–193 |
| 34 | Phenethyl | 92–94 |
| 35 | 1-Adamantyl | 167–168 |
| 36 | 4-NO$_2$ phenyl | 208–209 |

TABLE 2

$$\text{R}_1\text{NHCNHR}_2 \atop \overset{S}{\|}$$

| Example | R$_1$ | R$_2$ | mp (°C.) |
|---|---|---|---|
| 37 | 3,4-diCl phenyl | CH$_3$(CH$_2$)$_5$ | oil |
| 38 | 3,4-diCl phenyl | CH$_3$ | 144–145 |
| 39 | 1-Naphthyl | CH$_3$(CH$_2$)$_5$ | 73–77 |
| 40 | Phenyl | CH$_3$(CH$_2$)$_5$ | 74–75 |

EXAMPLE 41

N,N'-Diundecylthiourea

Thiophosgene (10.9 mls, 0.14 moles) is added dropwise to a well stirred mixture of undecylamine (49.9 g, 0.29 moles) and water (400 mls). The mixture is heated to reflux following the addition. After 45 minutes the mixture is allowed to cool while potassium carbonate (20.0 g, 0.14 moles) is added in portions, and is then reheated to reflux. After three hours the mixture is cooled and the product is filtered off, triturated in 2N HCl, refiltered, rinsed with water, and dried. Recrystallization from ethylacetate gave the product (32.7 g) mp 70°–72° C.

The above is analogous to the procedure of Dyson. J. Chem. Soc. 125(1924)1702.

The following compounds are prepared by the method described in Example 41.

TABLE 3

$$\text{RNHCNHR} \atop \overset{S}{\|}$$

| Example | R | mp (°C.) |
|---|---|---|
| 42 | CH$_3$(CH$_2$)$_4$ | oil |
| 43 | CH$_3$(CH$_2$)$_5$ | oil |
| 44 | CH$_3$(CH$_2$)$_7$ | 53–55 |
| 45 | 1-Naphthyl | 228–230 |
| 46 | 3,4-di Cl phenyl | 160–161 |
| 47 | 3,4-di Br phenyl | 153–155 |
| 48 | 3,4,5-tri Cl phenyl | 176–178 |
| 49 | 4-Butylphenyl | 149–151 |
| 50 | 4-Decylphenyl | 132–134 |
| 51 | 3,4-Dimethylphenyl | used crude |
| 52 | 3,4,5-Trimethoxyphenyl | used crude |

EXAMPLE 53

N,N'-Didodecylthiourea

Thiophosgene (10.0 mls, 0.13 moles) is added dropwise to a stirred solution of dodecylamine (100 g, 0.54 moles) in toluene (210 mls). The mixture is heated to reflux for four hours then cooled in an icebath. The precipitate is filtered off, rinsed with toluene then ether, and dried, then treated with hot dilute HCl, rinsed with water and redried. Recrystallization from ethyl acetate gave the product (40.5 g), mp 75°–78° C.

The above method is disclosed in German Pat. No. 2 209 822.

EXAMPLE 54

Methyl[3-cyclohexyl-2-(cyclohexylimino)-4-oxo-5-thiazolidinylidene]acetate

A mixture of N,N'-dicyclohexylthiourea (10.0 g, 42 mmoles) and dimethylacetylenedicarboxylate (7.8 g, 55 mmoles) in methanol (100 mls) is stirred at room temperature for 16 hours, then warmed on a steambath for 45 minutes and cooled. The precipitate is filtered off, rinsed with cold methanol and dried. This gave the product as white crystals, (11.3 g), mp 97°–98° C.

The following compounds are prepared by the method described in Example 54.

TABLE 4

| Example | R$_1$ and R$_2$ | mp (°C.) |
|---|---|---|
| 55 | 4-Nitrophenyl | 219–228 |
| 56 | 4-Decylphenyl | 52–53 |
| 57 | 4-Methoxyphenyl | 95–99 |
| 58 | 4-Methylphenyl | 79–80 |
| 59 | 3-Methylphenyl | 112–113 |
| 60 | 2-Methoxyphenyl | 138–140 |
| 61 | 3-Methoxyphenyl | 147–148 |
| 62 | 4-Methoxyphenyl | 97–99 |

When tested by the procedures in a leukotriene receptor binding assay (RBL-1) as described by Bruns et al cited above, the compounds of the Formula I as defined in the present invention have the indicated activity as shown in Table 5 as $IC_{50}$ values expressed in $\mu Ms$ (micromolar).

TABLE 5

| Example | RBL-1 IC50 ($\mu M$) |
|---|---|
| 2 | >100 |
| 8 | >100 |
| 9 | >100 |
| 3 | 15.4 |
| 4 | 24.5 |
| 18 | 12.7 |
| 1 | 19.0 |
| 19 | >100 |
| 16 | >100 |
| 20 | >100 |
| 25 | 62.5 |
| 22 | 18.9 |
| 21 | 15.6 |
| 10 | >100 |
| 7 | >100 |
| 24 | >100 |
| 6 | >100 |
| 23 | 13.1 |
| 15 | >100 |
| 17 | 10.3 |
| 13 | 39.2 |
| 11 | 12.2 |
| 12 | >100 |

Accordingly, the present invention also includes a pharmaceutical composition for treating asthma or allergies comprising an effective amount of a compound of the Forumula I as defined above together with a pharmaceutically acceptable carrier.

The present invention further includes a method for treating asthma or allergies in mammals particularly humans suffering therefrom comprising administering to such mammals, particularly humans, either orally or parenterally a corresponding pharmaceutical composition containing a compound of Formula I as defined above in appropriate unit dosage form.

For preparing pharmaceutical compositions from the compounds of Formula I described by this invention, inert, pharmaceutically acceptable carriers can be either solid or liquid. Solid form preparations include powders, tablets, dispersible granules, capsules, cachets, and suppositories. A solid carrier can be one or more substances which may also act as diluents, flavoring agents, solubilizers, lubricants, suspending agents, binders or tablet disintegrating agents; it can also be encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby to solidify.

Liquid form preparations include solutions, suspensions, and emulsions. As an example may be mentioned water or water propylene glycol solutions for parenteral injection. Liquid preparations can also be formulated in solution in aqueous polyethylene glycol solution. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water with viscous material, i.e., natural or synthetic gums, resins, methylcellulose, sodium carboxymethylcellulose, and other well-known suspending agents.

Also included are solid form preparations which are intended to be converted, shortly before use, to liquid form preparations for either oral or parenteral administration. Such liquid forms include solutions, suspensions, and emulsions. These particular solid form preparations are most conveniently provided in unit dose form and as such are used to provide a single liquid dosage unit. Alternately, sufficient solid may be provided so that after conversion to liquid form, multiple individual liquid doses may be obtained by measuring predetermined volumes of the liquid form preparation as with a syringe, teaspoon, or other volumetric container. When multiple liquid doses are so prepared, it is preferred to maintain the unused portion of said liquid doses at low temperature (i.e., under refrigeration) in order to retard possible decomposition. The solid form preparations intended to be converted to liquid form may contain, in addition to the active material, flavorants, colorants, stabilizers, buffers, artificial and natural sweeteners, dispersants, thickeners, solubilizing agents, and the like. The liquid utilized for preparing the liquid form preparation may be water, isotonic water, ethanol, glycerine, propylene glycol, and the like as well as mixtures thereof. Naturally, the liquid utilized will be chosen with regard to the route of administration, for example, liquid preparations containing large amounts of ethanol are not suitable for parenteral use.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these in packaged form.

The quantity of active compound in a unit dose of preparation may be varied or adjusted from 10 mg to 500 mg preferably to 5 to 100 mg according to the particular application and the potency of the active ingredient. The compositions can, if desired, also contain other compatible therapeutic agents.

In therapeutic use as described above, the dosages may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter the dosage is increased by small increments until the optimum effect under the circumstances is reached. For convenience, the total daily dosage may be divided and administered in portions during the day if desired.

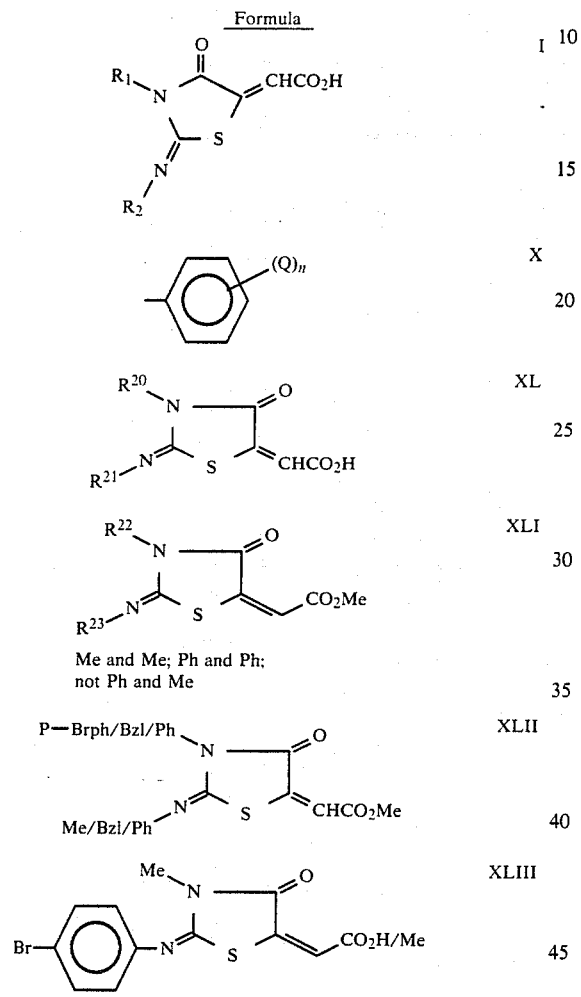

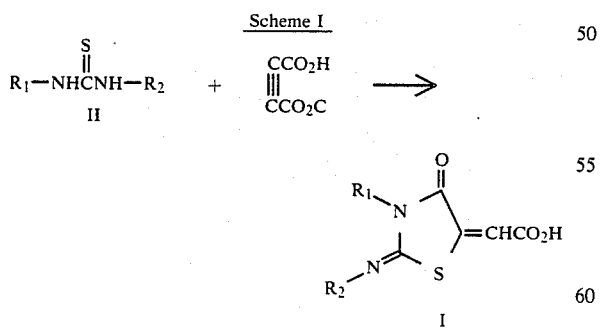

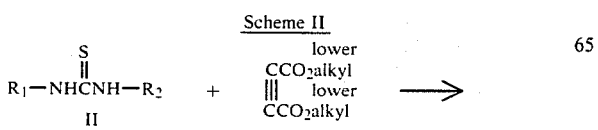

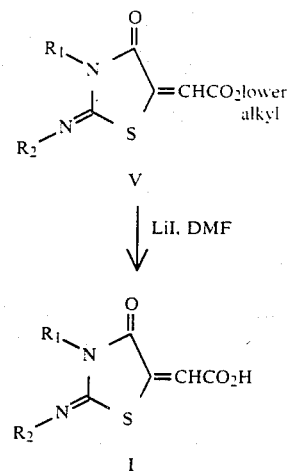

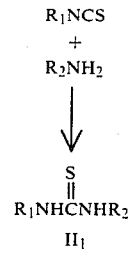

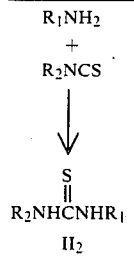

SCHEME III
R₁NCS
+
R₂NH₂
↓
$$R_1NHCNHR_2$$
II₁

SCHEME IV
R₁NH₂
+
R₂NCS
↓
$$R_2NHCNHR_1$$
II₂

What is claimed is:
1. A compound of formula

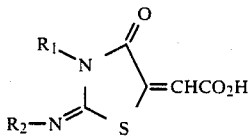

wherein R¹ and R² are the same or different and are (a) alkyl of from five to eight carbons, inclusive; (b) aryl having the structure

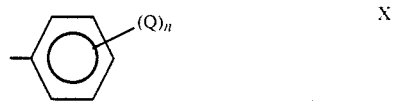

wherein n is (i) a number from zero to three, inclusive; (ii) where n is one then Q is alkyl of from one to four carbons, inclusive; or alkoxy of from one to four carbons, inclusive; and (iii) when n is two or three then Q is the same or different and is alkyl of from one to four carbons, inclusive; alkoxy of from one to four carbons; or halogen; (iv) where n is one, then Q is also nitro or amino optionally substituted by lower alkyl of from one to four carbons, inclusive;

(c) aralkyl wherein ar is aryl as defined above and alkyl is an alkylene of from one to four carbons, inclusive; or (d) cycloalkyl of from 3 to 7 carbon atoms, inclusive; or (e) naphthyl and pharmaceutically acceptable salts thereof, with the proviso that if $R_1$ and $R_2$ are the same then n cannot be zero and also with the proviso that when $R_1$ and $R_2$ are different then $R_2$ cannot be alkyl or aralkyl.

2. A compound of the claim 1 wherein $R_1$ and $R_2$ are the same and are (a) alkyl of from five to eight straight chain carbons, inclusive; (b) aryl of formula

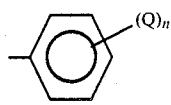 X wherein Q is halogen and n is as defined above.

3. A compound of claim 1 wherein $R_1$ and $R_2$ are different and are (a) alkyl of from five to eight straight chain carbons, inclusive; (b) aryl of formula

 X wherein n is a number of from zero to three, inclusive; and Q is alkyl of from one to four carbons, inclusive; or halogen; (c) aralkyl wherein ar is phenyl and alkyl is of from one to four carbons, inclusive; or (d) naphthyl.

4. A compound of claim 2 wherein $R_1$ and $R_2$ are alkyl of from five to eight carbons.

5. A compound of claim 3 wherein one of $R_1$ or $R_2$ is aryl having the Formula X as defined above wherein Q is halogen.

6. A compound of claim 3 wherein $R_1$ is alkyl of from five to eight carbons, inclusive, and $R_2$ is aryl of formula

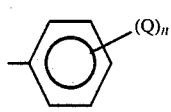 X wherein n is a number of from zero to three, inclusive, and Q is halogen; or 1-naphthyl.

7. A compound of claim 2 wherein $R_1$ and $R_2$ is aryl as defined in claim 2.

8. A compound of claim 4 wherein the embodiment is [3-octyl-2-(octylimino)-4-oxo-5-thiazolidinylidene]acetic acid.

9. A compound of claim 4 wherein the embodiment is [3-pentyl-2-(pentylimino)-4-oxo-5-thiazolidinylidene]acetic acid.

10. A compound of claim 4 wherein the embodiment is [3-hexyl-2-(hexylimino)-4-oxo-5-thiazolidinylidene]acetic acid.

11. A compound of claim 1 wherein the embodiment is [4-oxo-3-(3,4-dimethylphenyl)-2-[(3,4-dimethylphenyl)imino]-5-thiazolidinylidene]acetic acid.

12. A compound of claim 1 wherein the embodiment is [4-oxo-3-(3,4,5-trimethoxyphenyl)-2-[(3,4,5-trimethoxyphenyl)imino]-5-thiazolidinylidene]acetic acid.

13. A compound of claim 1 wherein the embodiment is [4-oxo-3-(4-methoxyphenyl)-2-[(4-methoxyphenyl)imino]-5-thiazolidinylidene]acetic acid.

14. A compound of claim 1 wherein the embodiment is [3-(2-methoxyphenyl)-2-[(2-methoxyphenyl)imino]-4-oxo-5-thiazolidinylidene]acetic acid.

15. A compound of claim 6 wherein the embodiment is [2-[(2,4-dichlorophenyl)imino]-3-hexyl-4-oxo-5-thiazolidinylidene]acetic acid.

16. A compound of claim 6 wherein the embodiment is [3-hexyl-4-oxo-2-(phenylimino)-5-thiazolidinylidene]acetic acid.

17. A compound of claim 1 wherein the embodiment is [3-(1-naphthyl)-2-[1-naphthyl)imino]-4-oxo-5-thiazolidinylidene]acetic acid.

18. A compound which is [3-undecyl-2-(undecylimino)-4-oxo-5-thiazolidinylidene]acetic acid.

19. A compound of claim 6 wherein the embodiment is [3-hexyl-2-[(1-naphthyl)imino]-4-oxo-5-thiazolidinylidene]acetic acid.

20. A compound of claim 4 wherein the embodiment is [3-heptyl-2-(heptylimino)-4-oxo-5-thiazolidinylidene]acetic acid.

21. A compound which is [3-decyl-2-(decylimino)-4-oxo-5-thiazolidinylidene]acetic acid.

22. A compound which is [3-dodecyl-2-(dodecylimino)-4-oxo-5-thiazolidinylidene]acetic acid.

23. A compound of claim 7 wherein the embodiment is [4-oxo-3-(3,4-dichlorophenyl)-2-(3,4-dichlorophenyl)imino-5-thiazolidinylidene]acetic acid.

24. A compound of claim 7 wherein the embodiment is [4-oxo-3-(3,4-dibromophenyl)-2-(3,4-dibromophenyl)imino-5-thiazolidinylidene]acetic acid.

25. A compound of claim 7 wherein the embodiment is [4-oxo-3-(3,4,5-trichlorophenyl)-2-(3,4,5-trichlorophenyl)imino-5-thiazolidinylidene]acetic acid.

26. A compound of claim 1 wherein the embodiment is [3-(3-methoxyphenyl)-2-(3-methoxyphenyl)imino-4-oxo-5-thiazolidinylidene]acetic acid.

27. A compound of claim 1 wherein the embodiment is [3-cyclohexyl-2-(3-cyclohexyl)imino-4-oxo-5-thiazolidinylidene]acetic acid.

28. A compound of claim 1 wherein the embodiment is [4-oxo-3-(4-methylphenyl)-2-[(4-methylphenyl)imino]thiazolidinylidene]acetic acid.

29. A compound of claim 1 wherein the embodiment is [4-oxo-3-(3-methylphenyl)-2-[(3-methylphenyl)imino]-5-thiazolidinylidene]acetic acid.

30. A compound of claim 1 wherein the embodiment is [3-(4-nitrophenyl)-2-(4-nitrophenylimino)-4-oxo-5-thiazolidinylidene]acetic acid.

31. A compound which is [3-(4-decylphenyl)-2-(4-decyclphenylimino)-4-oxo-5-thiazolidinylidene]acetic acid.

32. A pharmaceutical composition having a unit dosage comprising a compound of Formula I of claim 1; and pharmaceutically acceptable salts thereof in admixture with a pharmaceutically acceptable carrier.

* * * * *